United States Patent [19]
Schmidt

[11] Patent Number: 4,790,833
[45] Date of Patent: Dec. 13, 1988

[54] BAG OF PLASTIC FILM FOR COLLECTING DISCHARGES FROM HUMAN OR ANIMAL BODIES VIA DRAINS

[75] Inventor: Richard Schmidt, Bagsvaerd, Denmark

[73] Assignee: Coloplast A/S, Denmark

[21] Appl. No.: 59,877

[22] PCT Filed: Sep. 26, 1986

[86] PCT No.: PCT/DK86/00107
§ 371 Date: May 22, 1987
§ 102(e) Date: May 22, 1987

[87] PCT Pub. No.: WO87/01932
PCT Pub. Date: Apr. 9, 1987

[30] Foreign Application Priority Data

Sep. 27, 1985 [DK] Denmark .............................. 4381/85

[51] Int. Cl.[4] .............................................. A61M 1/00
[52] U.S. Cl. .................................... 604/317; 604/332
[58] Field of Search ................. 604/277, 332–345, 604/317, 318; 383/35; 428/167; 264/292; 128/767

[56] References Cited

U.S. PATENT DOCUMENTS

| | | | |
|---|---|---|---|
| 2,496,175 | 1/1950 | Porry | 604/340 |
| 2,504,872 | 4/1950 | Perry | 128/283 |
| 2,638,898 | 5/1953 | Perry | 128/283 |
| 3,220,544 | 11/1965 | Lovell | 264/292 |
| 3,830,235 | 8/1974 | Marsan | 604/277 |
| 4,197,849 | 4/1980 | Bostick | 4/144.3 |
| 4,553,967 | 11/1985 | Ferguson et al. | 604/317 |
| 4,661,100 | 4/1987 | Rechsteiner | 604/317 |

Primary Examiner—C. Fred Rosenbaum
Assistant Examiner—J. L. Kruter
Attorney, Agent, or Firm—Ostrolenk, Faber, Gerb & Soffen

[57] ABSTRACT

A plastic bag for collecting discharges via a drain, especially from operation wounds, from, e.g., the thoracic and abdominal cavities. The bag is somewhat similar to an ostomy bag but differs in that a portion of its front wall has an increased surface area and reduced material thickness by being processed to form a film blister. This blister area allows a grip on the drain protruding into the bag through an aperture in its rear wall. The grip provided by the blister area makes it possible to manipulate the drain, notably to pull it gradually out from the body, without exposing the operation wound to any risk of infection.

8 Claims, 4 Drawing Sheets

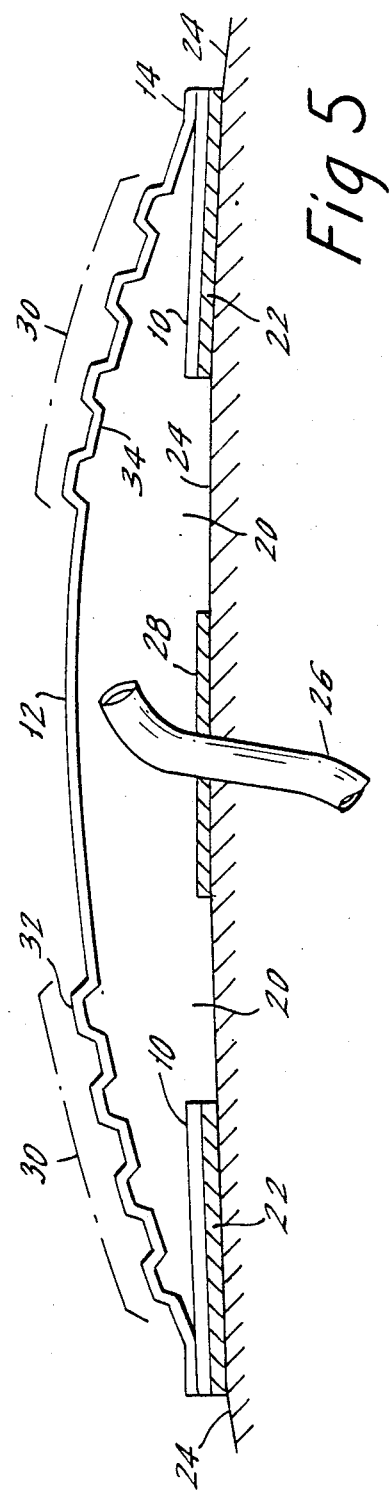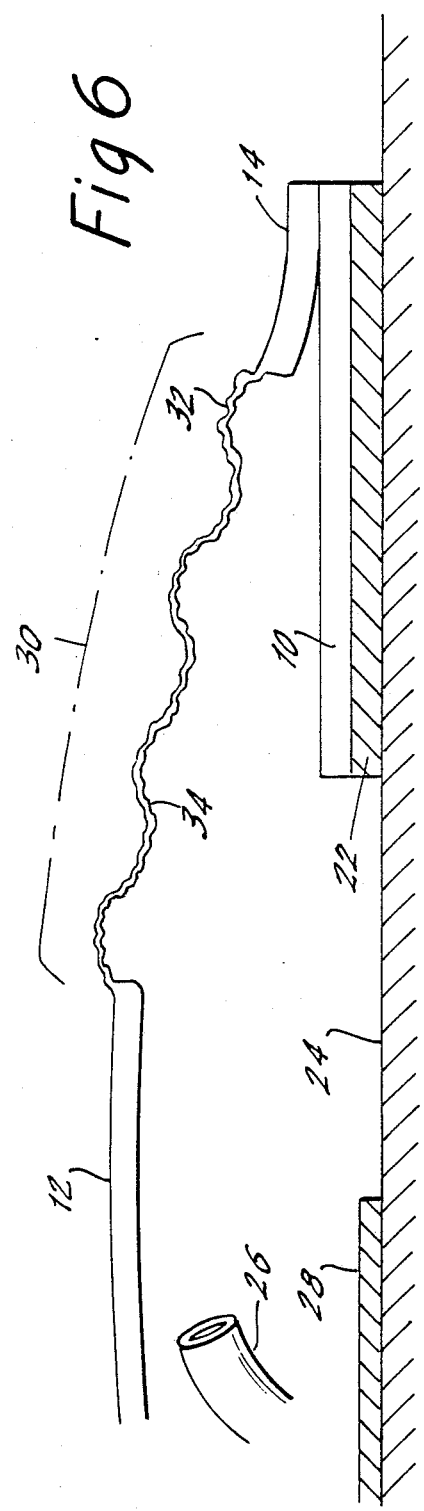

BAG OF PLASTIC FILM FOR COLLECTING DISCHARGES FROM HUMAN OR ANIMAL BODIES VIA DRAINS

FIELD OF THE INVENTION

The present invention relates to a bag of plastic film for collecting discharges from the human or animal body via a drain, the bag consisting of a rear wall and a front wall sealed to each other along the edges, the rear wall being provided with an aperture adapted to receive the drain; means around that aperture for attaching the bag to the body surface around a body opening, usually a surgically made incision, through which the drain carries the discharges from the body to the bag; and optionally a closable discharge opening in the bottom of the bag. The drain may be corrugated or tubular, e.g. a catheter or a plastic hose.

BACKGROUND OF THE INVENTION

There is known a very large variety of bags for collecting feces from an ostomy opening or incontinent anus, or for collecting urine. They have a front wall and a rear wall through an aperture in which the discharges from the body pass directly into the bag; the aperture is usually surrounded by some means for—frequently adhesive—attaching the bag to the body.

It is known to use such or similar bags—in many cases simply an ostomy bag—for collecting pus or other wound secretions arising in body cavities, e.g. in the abdominal or thoracic cavity after surgical operations. The discharge thereof differs from the discharge of intestinal excretions or urine through natural or artificial body openings by taking place via some kind of a drain.

From U.S. Pat. No. 3,954,105 there is known a drainage system consisting of a drain inserted into a wound or an incision in a body surface, and a collecting bag having an opening in a rear wall, said opening at its edges provided with suitable, normally adhesive means for attaching the bag around the wound or incision. Opposite the opening in the rear wall there is also an opening in the front wall through which the drain may be manipulated and optionally replaced. The opening in the front wall is surrounded by suitably rigid wall parts to which a rigid or semi-rigid, normally dome-shaped cap may be affixed; it is normally affixed to the front wall of the bag and is preferably transparent so as to allow inspection of the drain through the cap, which is removed when the drain is to be manipulated. Besides being relatively costly, the construction has the disadvantage that it is difficult to maintain sterile conditions when the drain is to be manipulated, precisely because the cap must be taken off.

From FR patent specification No. 1,513,360 there is known a catheter system wherein a thin plastic bag is secured to a holder for a cannula adapted to prick a hole in the skin and a vein and through which the catheter is inserted into the vein, said plastic bag surrounding the catheter prior to the insertion. The bag is removed when the catheter has been inserted since its purpose is to ensure sterility during the insertion but not to collect material which might flow out through the catheter.

The opening in the body through which a wound drain has been positioned is usually formed surgically; it may be the very surgically formed opening which has been used for the surgical operation, or a separate incision placed in the immediate proximity thereof. When the drain has been placed and possibly fixed in a definite position, the collecting bag is positioned and is often, like ostomy bags, adhesively attached to the skin around the site of the insertion of the drain.

In the drainage of operation wounds, it is very important that the drain does not slide into the body. It is also important that it does not unintentionally slide out of it. And finally, it is in most cases desirable that one can remove the drain gradually, e.g. at 2–3 cm per day, in order to thereby render a progressive tissue consolidation possible.

When the bag has been positioned it should preferably not be taken away before the drain and the bag are to be removed definitively because any temporary removal of the bag involves a risk of infecting the operation wound. In other words, it is desirable to be able to manipulate the drain from outside the bag, without removing the bag or altering its position. With known bags such a manipulation of drains from outside causes considerable difficulties. The two walls of the bag are identical apart from the opening through which excretions enter it, have identical outer shape and in the flat state of the bag lie smoothly against one another. If with the fingers or a tool one grips a portion of the front wall of the bag opposite the drain and hereby grips the drain in order to manipulate it, a pull will necessarily be caused in the front wall of the bag and the edge portion where it is welded to the rear wall, and the latter will bend towards the manipulating person and thereby exert a pull in the means with which it is attached to the skin of the patient. Apart from this, the manipulation in itself is difficult under these circumstances and it is impeded further by the fact that the bag film is smooth and therefore easily slides relative the drain during the manipulation thereof, which may render a precise manipulation difficult.

BRIEF DESCRIPTION OF THE INVENTION

It is the object of the invention to avoid these drawbacks and provide a bag of the kind defined in the opening paragraph, allowing an easy manipulation of a drain.

This is achieved if according to the invention the upper part of the front wall in an area opposite the aperture in the rear wall and optionally its surroundings has been processed to form a film blister of increased surface area and reduced material thickness compared to the surface area and thickness without such processing.

Processing to form film blisters is a well-known technique and does not as such constitute a part of the invention. The blister forming may for instance take place by deep drawing, by means of vacuum or compressed air, by upsetting, by pressing or by any other known film blister forming technique.

When a film blister area as described has been formed, it is by manipulation possible without a substantial pull in the edges of the film blister portion to grip the drain and displace it longitudinally to a desired degree, optionally by a number of pulls.

It should be noted that in some cases the drain is sutured to the body wall around it. If the suture has been tied by an easily accessible and simple knot the bag according to the invention may be used in such a case because, via the deep drawn portion of the bag wall, one will be able to untie such a knot and later tie it anew. However, the bag according to the invention is particularly well suited for use in cases where the drain is attached to the body surface by means of a particular fixation device.

According to the invention the film blister pattern may be wavy, seen in cross section of the bag.

According to the invention it is advantageous if the film blister has a comparatively coarse structure and has been overlaid by a finer blister structure.

BRIEF DESCRIPTION OF THE DRAWINGS

In the following, the bag according to the invention is described more fully with reference to the drawings, in which

FIG. 5 is an enlargement of FIG. 2, showing the feature of the film material being thinner in the blistered area than outside the blistered area; and FIG. 6 is an enlargement of the right side portion of FIG. 2, modified to show the feature of a finer blister overlaying a course blister.

DETAILED DESCRIPTION OF PREFERRED EMBODIMENTS

Figure 1:
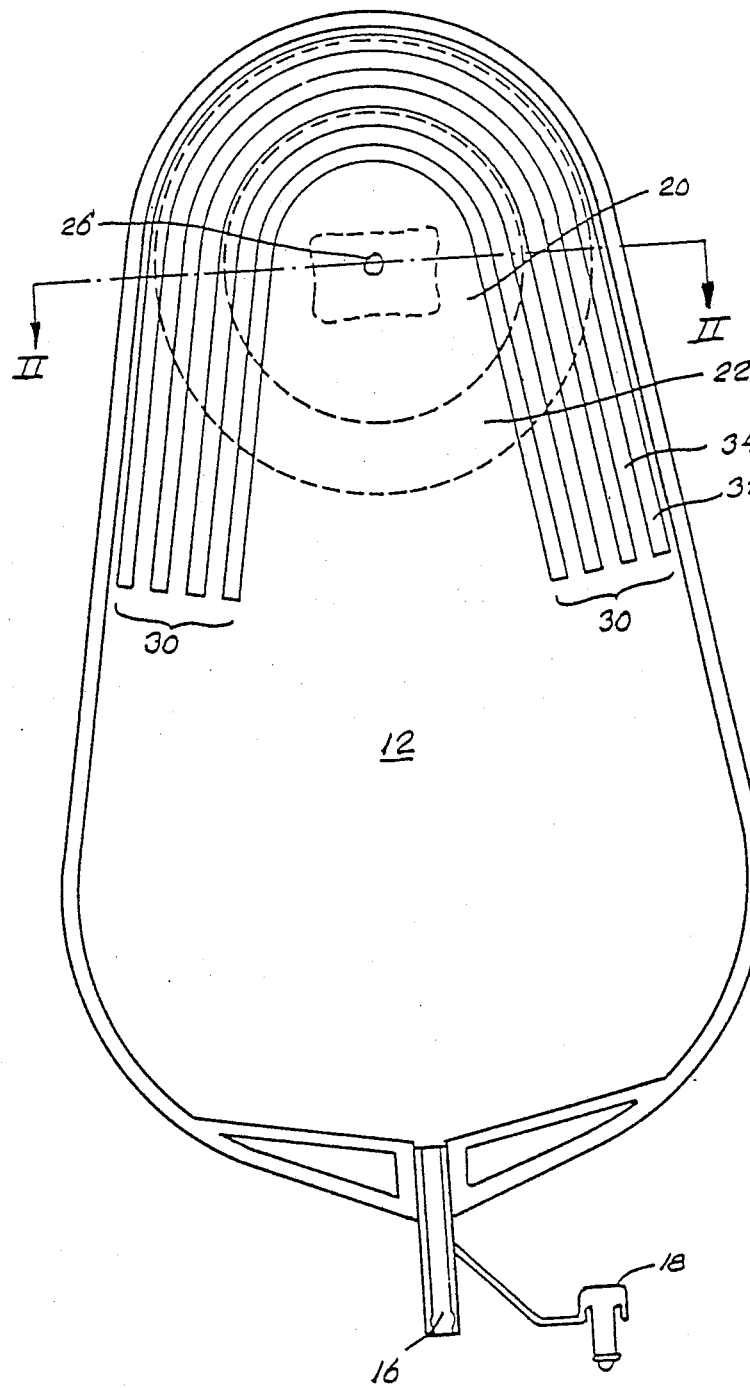
FIG. 1 shows one preferred embodiment of the bag according to the invention in its flat condition, seen from the front wall, FIG. 2 a section along line II—II in FIG. 1, yet with the bag in a faintly inflated condition and attached to the skin of a patient, FIG. 3 another preferred embodiment in flat condition, FIG. 4 a section along line IV—IV in FIG. 3 with the bag in a faintly inflated condition.

The bag according to the invention has a rear wall 10 and a front wall 12. They are firmly secured to each other at the edges by a heat sealing seam 14. In the lower part the bag in the embodiments shown has a discharge opening 16 which may be closed by means of for instance a stopper 18. If desired, the discharge opening may be omitted.

Figure 2:
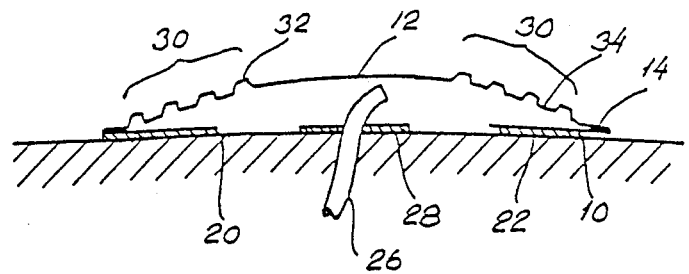

In the rear wall there is an opening 20 surrounded by an annular fastening means 22 by the aid of which the bag may be attached to the skin 24 of a patient around a surgically formed opening through which a drain 26 is extending. In FIGS. 1-2, the fastening means 22 is a flange adhered to a ring made of a skin-friendly material which is adhesive on both sides, expediently of the kinds described in U.S. Pat. Nos. 4,231,369 and 4,367,732. The drain is fixed in a desired position by means of a schematically shown fixation device 28. This is attached separately to the skin around the operation wound, has some kind of connection directly to the bag according to the invention and does not constitute a part of the present invention.

The rear wall 10 of the bag in the embodiment shown is substantially smooth and flat and is essentially constructed as the rear wall in numerous known ostomy bags.

In contradistinction hereto the front wall of the bag is different because a portion 30 thereof by processing in some manner known per se has been formed into a so-called film blister. By this treatment, there has been formed a number of waves (as shown in FIG. 1 four, in FIG. 3 five) in the form of bulges 32, projecting from the plane of the front wall, alternating with depressions 34.

Figure 3:
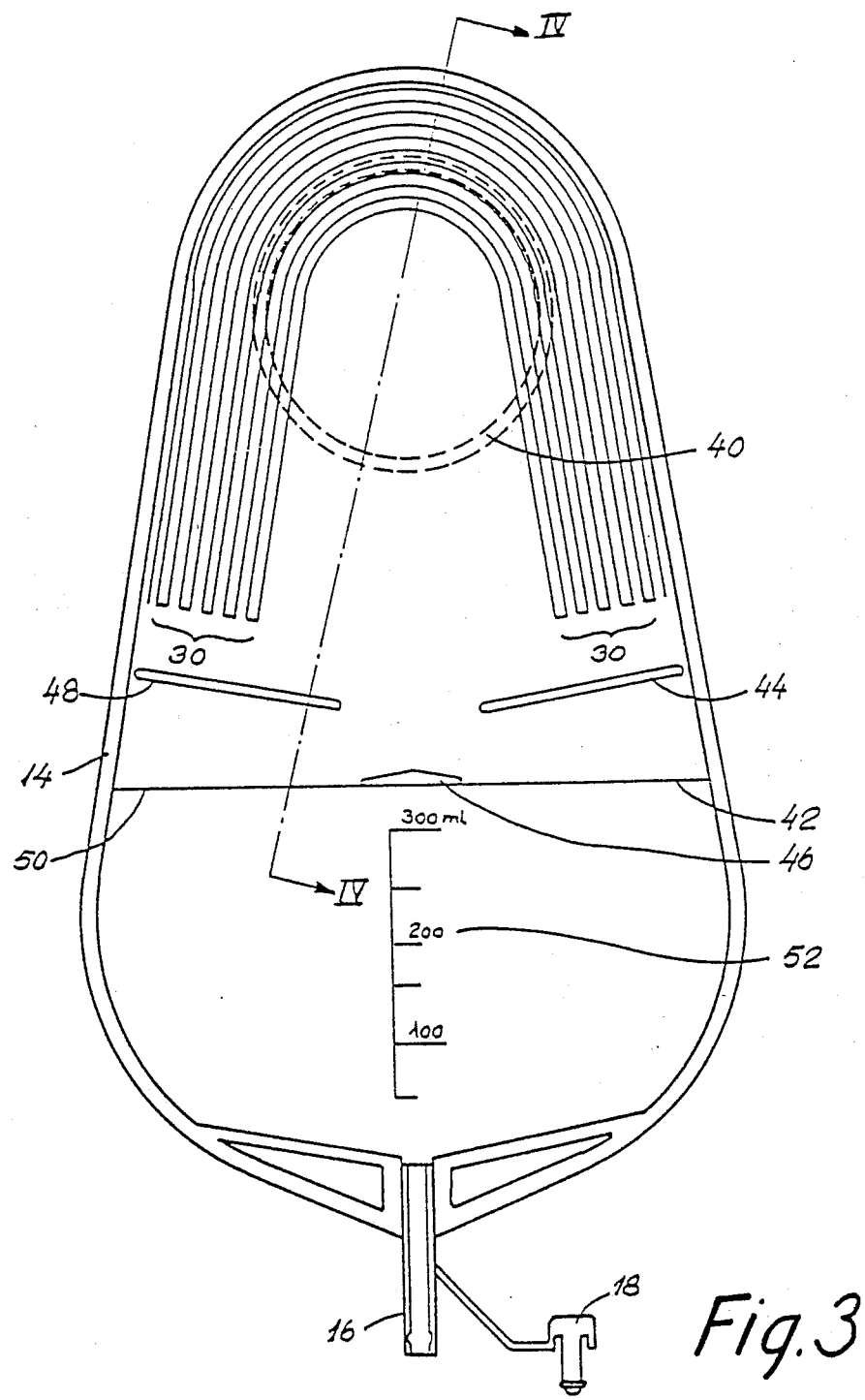

According to the invention, these waves preferably—and as shown in FIGS. 1 and 3—seen in the plane of the bag wall, form a pattern of a number of substantially straight lines substantially parallel to the lateral edges of the bag, whereby each straight line parallel to one lateral edge is connected to a corresponding straight line parallel to the other lateral edge of the bag by a substantially circular arc.

Many other configurations are also possible, e.g. as a number of circles or a number of straight lines forming angles, e.g. right angles with each other. However, straight lines intersecting each other have been found to be less suitable because undesired tensions may arise where the lines meet.

By the said processing to form the film blister portion, the portion in question obtains a considerably larger area than before the processing and at the same time the film in the area in question becomes thinner and thereby more supple. It is therefore readily possible by a grip on the exterior of the bag's front wall by the fingers or a suitable tool to grip and manipulate the drain 26 in a desired manner without any necessity of removing the bag from its position around the operation wound and hereby there is achieved a substantially improved safety against infections of the wound. The feature of the film material being thinner in the blistered area 30 than outside the blistered area is best shown in FIG. 5, which is an enlargement of FIG. 2, wherein like numbers represent like elements.

If desired, a limited area of the rear wall of the bag may according to the invention be processed into a film blister, whereby the possiblities of manipulating may be further increased.

The bag may be made of any, preferably transparent plastic film material of the kinds used, e.g., for making colostomy bags. Thus, the material may for instance be polyethylene, polypropylene or polyvinyl chloride. The thickness of the film material prior to the deep drawing or other processing to form the bulges and depressions 32,34 will be at least 40 μm and at most 150 μm, typically 60–80 μm. The degree of deep drawing may vary within a wide range and depends on the tear strength, breaking strength, elongation at break and barrier properties. Expediently, the thickness in the deep drawn areas in many cases may be of the order of magnitude 20–40 μm.

Figure 4:
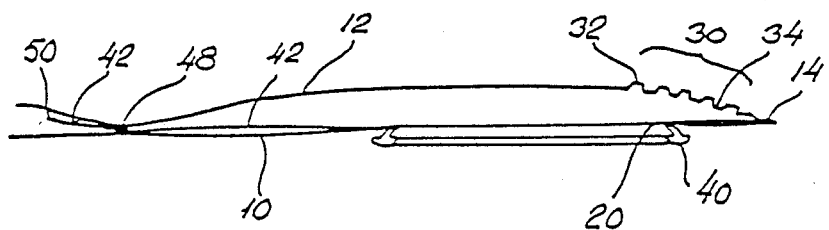

The collecting bag shown in FIGS. 3–4 mainly differs from that shown in FIGS. 1-2 by the means by which it is attached to the patient, and by means (as described in U.S. Pat. No. 4,604,095 to counteract return flow of wound secretions.

The bag according to FIGS. 3–4 has a front wall 12 and a rear wall 10. In the rear wall 10 there, is an aperture 20 for the inflow of wound secretions and for placing a fixation device, not shown, for a drain. The opening 20 is surrounded by a coupling ring 40; this may be any known coupling ring but is very conveniently constructed as described in U.S. patent application Ser. No. 867,523, filed May 27, 1986. The coupling ring 40 is adapted to co-operate with another coupling ring (not shown) which by the aid of an adhesive material, e.g. of the above-mentioned skin-friendly kind, is adhered to the skin around the operation wound. The other coupling ring is expediently adapted to hold the wound drain.

Besides the front wall 12, which is provided with a film blister portion 30, and the rear wall 10, the bag shown in FIGS. 3–4 has a partition 42, normally of the same material as the front and rear walls. In the upper part of the bag, the partition 42 is secured to the rear wall 10, expediently in the area where the ring 40 is situated. The partition 42 only extends from the upper part to approximately the middle or a little below the middle of the bag, as is seen both in FIG. 3 and FIG. 4. In its lower part it is secured to the front wall 12 of the bag by means of three heat sealing seams 44, 46 and 48. The seams 44 and 48 are symmetrical with respect to the longitudinal middle plane of the bag and are spaced from the lower, substantially free edge of the partition 42. Opposite the interspace between the seams 44 and 48, but closer to and preferably (as shown) just at the edge 50 of the partition the third heat sealing seam is situated. The wound secretion can flow through the interspaces between the heat sealing seams 44,46 and 48,46 down to the free bag compartment below the lower edge 50 of the partition, but only with difficulty flow back to the opening 20. The arrangement with the partition 42 and the heat sealings 44,46,48 therefore functions as an effective non-return valve.

The bag shown in FIG. 3 is provided with a gauge for collected secretions.

Even after the blister processing the bag film may be rather smooth, and as the drain easily becomes moistened by the outflowing wound secretion, the smoothness in unlucky cases may impede a precize manipulation. This may be counteracted by a kind of roughening of the film blister portion of the front wall of the bag. The thickness of material will normally be too small to allow a normal napping without the risk of perforating the film. But according to the invention, the roughening can take place by a "blister processing in the blister", whereby the comparatively coarse primary film blister described above may be overlaid by a finer blister structure. This embodiment of the invention is shown in FIG. 6, which is an enlarged view of enlarged view of the right side portion of FIG. 2, modified to show the detail of the fine blistered structure overlaying a comparatively course blister structure.

I claim:

1. A bag of plastic film for collecting discharges from human and animal bodies via drains, the bag consisting of a rear wall and a front wall sealed to each other along the peripheral edges, the rear wall being provided with an aperture adapted to receive a drain; means around said aperture for attaching the bag to the body surface around a body opening through which the drain carries the discharges from the body to the bag; wherein the upper part of the front wall in at least an area opposite the aperture in the rear wall has been processed to form a supple film blister means to allow the user to manipulate a drain, said film blister means being of increased surface area and reduced material thickness compared to the surface area and thickness without such processing.

2. A collecting bag according to claim 1, wherein the film blister pattern is wavy in cross-section.

3. A collecting bag according to claim 2, wherein the waves of the film blister in cross-section form a pattern of a number of substantially straight lines substantially parallel to lateral edges of the bag, each straight line parallel to one lateral edge being connected to a corresponding straight line parallel to the other lateral edge of the bag by a substantially circular arc.

4. A collecting bag according to claim 1, wherein the film blister has a comparatively coarse structure and has been overlaid with finer blister structure.

5. A bag of plastic film for collecting discharges from human and animal bodies via drains, the bag consisting of a rear wall and a front wall sealed to each other along the peripheral edges, the rear wall being provided with an aperture adapted to receive a drain; means around said aperture for attaching the bag to the body surface around a body opening through which the drain carries the discharges from the body to the bag, and a closable discharge opening in the bottom of the bag; wherein the upper part of the front wall in at least an area opposite the aperture in the rear wall has been processed to form a supple film blister means to allow the user to manipulate a drain, said film blister means being of increased surface area and reduced material thickness compared to the surface area and thickness without much processing.

6. A collecting bag according to claim 5, wherein the film blister has a comparatively coarse structure and has been overlaid with a finer blister structure.

7. A collecting bag according to claim 5, wherein the film blister pattern is wavy in cross-section.

8. A collecting bag according to claim 7, wherein the waves of the film blister in cross-section form a pattern of a number of substantially straight lines substantially parallel to lateral edges of the bag, each straight line parallel to one lateral edge being connected to a corresponding straight line parallel to the other lateral edge of the bag by a substantially circular arc.

* * * * *